US008647646B2

(12) United States Patent
Frenkel et al.

(10) Patent No.: US 8,647,646 B2
(45) Date of Patent: *Feb. 11, 2014

(54) CRYSTALS OF LAQUINIMOD SODIUM, AND PROCESS FOR THE MANUFACTURE THEREOF

(75) Inventors: Anton Frenkel, Netanya (IL); Eduard Gurevich, Petach Tikva (IL); Avital Laxer, Tel Aviv (IL)

(73) Assignee: Teva Pharmaceutical Industries, Ltd., Petach-Tikva (IL)

(*) Notice: Subject to any disclaimer, the term of this patent is extended or adjusted under 35 U.S.C. 154(b) by 0 days.

This patent is subject to a terminal disclaimer.

(21) Appl. No.: 13/011,233

(22) Filed: Jan. 21, 2011

(65) Prior Publication Data

US 2011/0112141 A1 May 12, 2011

Related U.S. Application Data

(62) Division of application No. 11/583,282, filed on Oct. 18, 2006, now Pat. No. 7,884,208.

(60) Provisional application No. 60/728,657, filed on Oct. 19, 2005.

(51) Int. Cl.
*C07D 215/00* (2006.01)
*A01N 43/42* (2006.01)
*A61K 31/47* (2006.01)

(52) U.S. Cl.
USPC ............................ 424/400; 514/312; 546/156

(58) Field of Classification Search
USPC ........................................... 514/312; 546/156
See application file for complete search history.

(56) References Cited

U.S. PATENT DOCUMENTS

| 3,024,257 | A | 3/1962 | Millar at al. |
| 4,107,310 | A | 8/1978 | Allais et al. |
| 4,547,511 | A | 10/1985 | Eriksoo et al. |
| 4,628,053 | A | 12/1986 | Fries et al. |
| 4,738,971 | A | 4/1988 | Eriksoo et al. |
| 5,716,638 | A | 2/1998 | Touitou et al. |
| 5,912,349 | A | 6/1999 | Sih et al. |
| 6,077,851 | A * | 6/2000 | Bjork et al. ............ 514/312 |
| 6,121,287 | A | 9/2000 | Bjork et al. |
| 6,133,285 | A | 10/2000 | Bjork et al. |
| 6,307,050 | B1 | 10/2001 | Kwiatkowski et al. |
| 6,395,750 | B1 | 5/2002 | Hedlund et al. |
| 6,593,343 | B2 | 7/2003 | Bjork et al. |
| 6,605,616 | B1 | 8/2003 | Bjork et al. |
| 6,613,574 | B2 | 9/2003 | Shimada |
| 6,802,422 | B2 | 10/2004 | Kalvelage et al. |
| 6,875,869 | B2 | 4/2005 | Jansson et al. |
| 7,560,557 | B2 | 7/2009 | Jansson et al. |
| 7,589,208 | B2 | 9/2009 | Jansson et al. |
| 8,178,127 | B2 | 5/2012 | Safadi et al. |
| 2002/0173520 | A1 | 11/2002 | Bjork et al. |
| 2003/0087929 | A1 | 5/2003 | Kimura et al. |
| 2003/0119826 | A1 | 6/2003 | Manning et al. |
| 2003/0124187 | A1 | 7/2003 | Mention et al. |
| 2004/0247673 | A1 | 12/2004 | Fergione et al. |
| 2004/0253305 | A1 | 12/2004 | Luner et al. |
| 2005/0192315 | A1* | 9/2005 | Jansson et al. ............ 514/312 |
| 2005/0215586 | A1 | 9/2005 | Jansson et al. |
| 2005/0271717 | A1 | 12/2005 | Berchielli et al. |
| 2007/0088050 | A1 | 4/2007 | Frenkel et al. |
| 2007/0280891 | A1 | 12/2007 | Tamarkin et al. |
| 2007/0293537 | A1 | 12/2007 | Patashnik et al. |
| 2009/0162432 | A1 | 6/2009 | Safadi et al. |
| 2009/0232889 | A1 | 9/2009 | Jansson et al. |
| 2010/0055072 | A1 | 3/2010 | Gant et al. |
| 2010/0322900 | A1 | 12/2010 | Tarcic et al. |
| 2011/0027219 | A1 | 2/2011 | Tarcic et al. |
| 2011/0034508 | A1 | 2/2011 | Hayardeny et al. |
| 2011/0118308 | A1 | 5/2011 | Frenkel et al. |
| 2011/0171270 | A1 | 7/2011 | Dixit et al. |
| 2011/0217295 | A1 | 9/2011 | Haviv et al. |
| 2011/0218179 | A1 | 9/2011 | Haviv et al. |
| 2011/0218203 | A1 | 9/2011 | Kaye et al. |
| 2011/0251235 | A1 | 10/2011 | Patashnik et al. |
| 2012/0010238 | A1 | 1/2012 | Piryatinsky |
| 2012/0010239 | A1 | 1/2012 | Fristedt |
| 2012/0142730 | A1 | 6/2012 | Tarcic et al. |
| 2012/0225124 | A1 | 9/2012 | Safadi et al. |

FOREIGN PATENT DOCUMENTS

| EP | 0497740 | 8/1992 |
| EP | 1073639 | 2/2001 |
| EP | 1095021 | 5/2001 |
| EP | 1097139 | 5/2001 |
| EP | 1511732 | 3/2005 |
| EP | 1720531 | 11/2006 |

(Continued)

OTHER PUBLICATIONS

Armarego et al. (2003). Purification of Laboratory Chemicals (5th Edition). Elsevier.*
Lab Manual (McMaster University. Chem2O06 Lab Manual: Expt. 1, Part B, Introduction, (1997-1998): p. 1-9).*
UMSL.edu (http://web.archive.org/web/20000305044205/http://www.umsl.edu/~orglab/pdffiles/practice.pdf. (Mar. 5, 2000)).*
PCT International Preliminary Report on Patentability issued Apr. 23, 2008 in connection with PCT International Application No. PCT/US2006/040925, filed Oct. 18, 2006.
PCT International Preliminary Report on Patentability issued Dec. 16, 2008 in connection with PCT International Application No. PCT/US2007/013721, filed Jun. 12, 2007.
PCT International Preliminary Report on Patentability issued Jun. 22, 2010 in connection with PCT International Application No. PCT/US2008/13890, filed Dec. 19, 2008.
PCT International Search Report issued Apr. 26, 2007 in connection with PCT International Application No. PCT/US2006/040925, filed Oct. 18, 2006.

(Continued)

*Primary Examiner* — Jeffrey S. Lundgren
*Assistant Examiner* — Chris Simmons
(74) *Attorney, Agent, or Firm* — John P. White; Gary J. Gershik; Cooper & Dunham LLP

(57) ABSTRACT

Disclosed is a process for the preparation of laguinimod sodium which removes the impurities after the salt formation step, thus resulting in crystals of higher purity as well as crystals having improved crystalline characteristics.

23 Claims, 3 Drawing Sheets

(56) References Cited

FOREIGN PATENT DOCUMENTS

| WO | WO 90/15052 | 12/1990 |
|---|---|---|
| WO | WO/99/15052 | 12/1990 |
| WO | WO/96/07601 | 3/1996 |
| WO | WO/99/55678 | 11/1999 |
| WO | WO/00/03991 | 1/2000 |
| WO | WO/00/03992 | 1/2000 |
| WO | WO 00/74654 | 12/2000 |
| WO | WO/01/30758 | 5/2001 |
| WO | WO/02/18343 | 3/2002 |
| WO | WO/03/106424 | 12/2003 |
| WO | WO 2004/013153 | 2/2004 |
| WO | WO/2005/041940 | 5/2005 |
| WO | WO/2005/074899 | 8/2005 |
| WO | WO/2007/146248 | 12/2007 |

OTHER PUBLICATIONS

PCT International Search Report issued Oct. 23, 2008 in connection with PCT International Application No. PCT/US2007/013721, filed Jun. 12, 2007.
PCT International Search Report issued Feb. 20, 2009 in connection with PCT International Application No. PCT/US2008/13890, filed Dec. 19, 2008.
Written Opinion of the International Searching Authority issued Apr. 26, 2007 in connection with PCT International Application No. PCT/US06/040925, filed Oct. 18, 2006.
Written Opinion of the International Searching Authority issued Oct. 23, 2008 in connection with PCT International Application No. PCT/US07/013721, filed Jun. 12, 2007.
Written Opinion of the International Searching Authority issued Feb. 20, 2009 in connection with PCT International Application No. PCT/US08/13890, filed Dec. 19, 2008.
Extended European Search Report issued Feb. 16, 2009 in connection with European Application No. 06826297.1.
Communication Pursuant to Article 94(3) EPC issued May 27, 2009 in connection with European Application No. 06826297.1.
Supplementary European Search Report issued Aug. 5, 2009 in connection with European Application No. 07809468.7.
Extended European Search Report issued Aug. 24, 2009 in connection with European Application No. 07809468.7.
Communication Pursuant to Article 94(3) EPC issued Dec. 15, 2009 in connection with European Application No. 07809468.7.
Communication Pursuant to Article 94(3) EPC issued May 7, 2010 in connection with European Patent Application No. 07809468.7.
Office Action issued May 25, 2010 by the Chinese Patent Office in connection with Chinese Patent Application No. 200680039201.6.
Examination Report issued Feb. 3, 2010 by the New Zealand Patent Office in connection with New Zealand Patent Application No. 567088.
Official Action issued Jun. 11, 2010 by the Russian Patent Office in connection with Russian Patent Application No. 2008119456.
First Office Action issued by the Ukrainian Patent Office in connection with Ukrainian Patent Application No. 2008 06003.
Examination Report issued Jul. 2, 2010 by the New Zealand Patent Office in connection with New Zealand Patent Application No. 573846.
Office Action issued Jun. 12, 2010 by the Chinese Patent Office in connection with Chinese Application No. 200780021677.1.
Office Action issued by the U.S. Patent and Trademark Office on Aug. 24, 2009 in connection with U.S. Appl. No. 11/811,810.
Office action issued by the U.S. Patent and Trademark Office on Jan. 6, 2010 in connection with U.S. Appl. No. 11/811,810.
Office Action issued by the U.S. Patent and Trademark Office on Jul. 21, 2010 in connection with U.S. Appl. No. 11/811,810.
Sep. 11, 2009 Communication in Response to Aug. 24, 2009 Office Action issued in connection with U.S. Appl. No. 11/811,810.
Apr. 6, 2010 Amendment in Response to Jan. 6, 2010 Office Action in connection with U.S. Appl. No. 11/811,810.

May 1, 2009 Response to Feb. 16, 2009 Extended European Search Report issued in connection with European Patent Application No. 06826297.1.
Jan. 13, 2010 Response to Dec. 15, 2009 Office Action issued in connection with European Patent Application No. 07809468.7.
Jun. 30, 2010 Response to First Ukrainian Office Action issued in connection with Ukrainian Patent Application No. 2008 06003.
Oct. 8, 2010 Response to Chinese Office Action issued May 25, 2010 in connection with Chinese Patent Application No. 200680039201.6.
Furniss, B. et al. (1989) "Recrystallization Techniques" Vogel's Text book of Practical Organic Chemistry, 5th ed., New York:John Wiley & Sons Inc.
Joseph Remington, Alfonso Gennaro. Remington's: the science and practice of pharmacy. 20 Ed. Lippincott Willaims & Wilkins, 2000.
Sandberg-Wollheim, T. Nederman, A Iinde (2005) "48-Week Open Safety Study . . . MS Patients" Therapy-Immunomodulation—Part II, Sep. 30, 2005, 15:30-17:00 (Abstract only).
Thompson, Claire (2003) "Investigating the Fundamentals . . . Microscopy" Thesis submitted to The University of Nottingham for the Degree of Doctor of Philosophy, May 2003.
Oct. 23, 2009 Communication Pursuant to 37 CFR 1.133(b) to Make of Record an Oct. 13, 2009 Interview With Examiner and Response Under 37 CFR 1.116 to Jul. 23, 2009 F.
U.S. Appl. No. 13/712,398, filed Dec. 12, 2012, Tarcic et al.
U.S. Appl. No. 13/785,511, filed Mar. 5, 2013, Haviv and Tarcic.
Apr. 8, 2011 Response to Feb. 3, 2010 Examination Report filed in connection with New Zealand Application No. 567088.
Nov. 22, 2012 Response to Nov. 1, 2012 Office Action filed in connection with Australian Patent Application No. 2006304672.
Feb. 22, 2012 Examination Report issued in connection with New Zealand Patent Application No. 567088.
Feb. 14, 2013 Office Action issued in connection with Canadian Patent Application No. 2,625,287.
Nov. 27, 2012 Amendment in Response to Jun. 27, 2011 Office Action filed in connection with U.S. Appl. No. 13/011,187.
Aug. 25, 2011 Response to May 24, 2011 Examination Report filed in connection with New Zealand Application No. 567088.
Jan. 7, 2013 Response to Jan. 11, 2012 First Examination Report in connection with Indian Patent Application No. 1035/MUMNP/2008.
Feb. 18, 2013 Communication Pursuant to Article 94(3) EPC issued in connection with European Patent Application No. 06826297.1.
May 1, 2013 Office Action issued in connection with Korean Patent Application No. 10-2008-7011727 (including an English language translation thereof).
Balbach S. et al. "Pharmaceutical evaluation of early development candidates: 'The 100 mg-approach,'" International Journal of Pharmaceutics, 275, pp. 1-12 (2004).
Bastin R.J. et al. "Salt Selection and Optimisation Procedures for Pharmaceutical New Chemical Entities", Organic Process & Development, 4, pp. 427-435 (2000).
Caira M.R, "Crystalline Polymorphism of Organic Compounds," Design of Organic Solids, Weber E et al. "ED" Springer, 1998.
Singhal D et al., "Drug Polymorphism and Dosage Form Design: A Practical Perspective," Advanced Drug Delivery Reviews, 56, pp. 335-347 (2004).
U.S. Appl. No. 13/560,872, filed Jul. 27, 2012, Gilgun and Tarcic.
U.S. Appl. No. 13/560,851, filed Jul. 27, 2012, Gilgun and Tarcic.
U.S. Appl. No. 13/650,060, filed Oct. 11, 2012, Hallak et al.
Communication Pursuant to Article 94(3) EPC issued Feb. 2, 2011 in connection with European Application No. 06826297.1 2102.
Apr. 27, 2011 Examination Report issued by the New Zealand Patent Office in connection with New Zealand Patent Application No. 567088.
Nov. 22, 2011 Office Action issued in connection with Australian Patent Application No. 2006304672.
May 24, 2011 Examination Report issued in connection with New Zealand Patent Application No. 592897.
Jan. 18, 2012 Examination Report issued in connection with Indian Patent Application No. 1035/MUMNP/2008.
Mar. 29, 2012 Examination Report issued in connection with New Zealand Patent Application No. 567088.
Apr. 24, 2012 Response to Mar. 29, 2012 Examination Report issued in connection with New Zealand Patent Application No. 567088.

(56) References Cited

OTHER PUBLICATIONS

Jun. 19, 2012 Office Action issued in connection with Japanese Patent Application No. 2008-536806 (with English language translation).
Aug. 31, 2012 Office Action issued in connection with Chinese Patent Application No. 200680039201.6 (with English language translation).
Nov. 15, 2012 Response to May 24, 2011 Examination Report issued in connection with New Zealand Patent Application No. 592897.
Office Action issued by the U.S. Patent and Trademark Office on May 13, 2008 in connection with U.S. Appl. No. 11/583,282.
Office Action issued by the U.S. Patent and Trademark Office on Jan. 10, 2008 in connection with U.S. Appl. No. 11/583,282.
Office Action issued by the U.S. Patent and Trademark Office on Oct. 16, 2008 in connection with U.S. Appl. No. 11/583,282.
Final Office Action issued by the U.S. Patent and Trademark Office on Jul. 23, 2009 in connection with U.S. Appl. No. 11/583,282.
Notice of Allowance issued by the U.S. Patent and Trademark Office on Sep. 23, 2010 in connection with U.S. Appl. No. 11/583,282.
Jun. 13, 2008 Communication in Response to May 13, 2009 Office Action issued in connection with U.S. Appl. No. 11/583,282.
Feb. 13, 2009 Communication in Response to Oct. 16, 2008 Office Action issued in connection with U.S. Appl. No. 11/583,282.
Jun. 27, 2012 Office Action issued in connection with U.S. Appl. No. 13/011,187.
May 5, 2011 Response to the Feb. 2, 2011 Communication Pursuant to Article 94(3) EPC issued in connection with European Patent Application No. 06826297.1.
May 17, 2011 Response to the Apr. 27, 2011 Examination Report issued in connection with New Zealand Patent Application No. 567088.
Dec. 16, 2011 Office Action issued connection with Chinese Patent Application No. 200680039201.6 (with English language translation).
Examination Report issued by the Australian Patent Office on Nov. 11, 2011 in connection with Australian Patent Application No. 2006304672.
Jansson, K. et al. (2005) "Synthesis and Reactivity of Laquinomod, a Quinoline-3-carboxamide: Intramolecular transfer of the enol proton . . . "J. Org. Chem. 71(4):1658-1667.
C. Elison et al. "Effect of Deuteration of N-CH3 Group on Potency and E Demethylation of Morphine" Science, Oct. 13, 1961, vol. 134, No. 3485, pp. 1078-1079 (abstract.
Helfenbein, "Isotopic Effect Study of Propofol Deuteration on the Metabolism, Activity, and Toxicity of the Anesthetic" J. Med. Chem., vol. 45, pp. 5806-5808 (2002).
U.S. Appl. No. 13/312,284, filed Dec. 6, 2011, Nora Tarcic et al.
PCT International Preliminary Report on Patentability issued Mar. 8, 2011 in connection with PCT International Application No. PCT/US2009/055692, filed Sep. 2, 2009.
PCT International Search Report issued Apr. 21, 2010 in connection with PCT International Application No. PCT/US2009/055692, filed Sep. 2, 2009.
PCT International Preliminary Report on Patentability issued Dec. 20, 2011 in connection with PCT International Application No. PCT/US2010/001759, filed Jun. 18, 2010.
Written Opinion of the International Searching Authority issued Aug. 19, 2010 in connection with PCT International Application No. PCT/US2010/001759.
Written Opinion of the International Searching Authority issued Apr. 21, 2010 in connection with PCT International Application No. PCT/US2009/055692, filed Sep. 2, 2009.
PCT International Search Report issued Nov. 21, 2011 in connection with PCT International Application No. PCT/US11/43383, filed Jul. 8, 2011.
Written Opinion of the International Searching Authority issued Nov. 21, 2011 in connection with PCT Intenrational Application No. PCT/US11/43383, filed Jul. 8, 2011.
Communication Pursuant to Article 94(3) EPC issued Feb. 2, 2011 in connection with European Application No. 06826297.1.
European Search Report completed Aug. 10, 2011 in connection with European Patent No. EP 09812145.
Apr. 27, 2011 Exam. Report issued by New Zealand Pat. Office in connection w/ N. Z. Pat. App. No. 567088, nat. stage PCT Int. App. No. PCT/US2006/040925, filed Oct. 18, 2006.
Office Action issued by the U.S. Patent and Trademark Office on Dec. 1, 2011 in connection with U.S. Appl. No. 13/166,210.
Apr. 8, 2011 Rsp to Jul. 2, 2010 Exam Rpt issued by N. Zealand Pat Office in connect'n w/ N. Z. Pat. App. No. 573846, nat. stage PCT Int App No. PCT/US2007/013721 filed Jun. 12, 2007.
May 5, 2011 Rsp to Feb. 2, 2011 Commun. Pursuant to Art. 94(3) EPC issued in connection with European Patent Application No. 06826297.1.
First Examination Report issued Jan. 11, 2012 in connection with Indian Patent Applicaton No. 1035/MUMNP/2008.
Nov. 30, 2011 Office Ation issued in connection with Chinese Patent Application No. 200780021677.1.
Dec. 16, 2011 Office Action issued connection with Chinese Patent Application No. 200680039201.6.
Brunmark et al. (2002) "The new orally active immunoregulator laquinimod (ABR-215062) effectively inhibits . . . autoimmune encephalomye." J. of Neuroimmunology, 13:163-172.
Tuvesson et al. (2005) "Cytochrome P450 3A4 is the Major Enzyme of Laquinimod, A Novel Immunomodulator" Drug Metabolism and Disposition 33(6):866-872.
Jönsson, Stig et al. "Synthesis and Biological Evaluation of New 1,2-Dihydro-4-hydroxy . . . " Journal of Medicial Chemistry, vol. 47, Mar. 16, 2004, pp. 2075-2088.
Jansson, K. et al. "Synthesis and Reactivity of Laquinomod, a Quinoline-3-carboxamide . . . " J. Org. Chem., Feb. 17, 2006, 71(4):1658-1667.
Boneschi M.F. et al. (2003) "Effects of glatiramer acetate on relapse rate and accumulated disability multiple sclerosis . . . " Mult. Scler. 9(4):349-55 (Abstract).
Polman C. et al. (2005) "Treatment with laquinimod reduces development of active MRI lesions in relapsing MS" Neurology 64(6):987-991.
Feb. 28, 2012 Response to Dec. 16, 2011 Office Action filed in connection with Chinese Patent Appl. No. 200680039201.6 (W/Engl. language draft).
Feb. 5, 2012 Response to Nov. 30, 2011 Office Action filed in connection with Chinese Patent Application No. 200780021677.1 (w/Engl. language draft).
Dec. 19, 2012 Response to Jun. 19, 2012 Office Action filed in connection with Japanese Patent Application No. 2008-536806 (w/ Engl. language draft).
Nov. 15, 2012 Response to Aug. 31, 2012 Office Action filed in connection with Chinese Patent Application No. 200680039201.6 (w/Engl. language draft).
Apr. 4, 2013 Office Action issued in connection with Mexican Patent Application No. MX/a/2008/005084 (w/Engl. language reporting letter).
Oct. 2, 2013 Second Office Action issued in connection with Mexican Patent Application No. MX/a/2008/005084 (w/Engl. language reporting letter).

\* cited by examiner

CRYSTALS OF LAQUINIMOD SODIUM, AND PROCESS FOR THE MANUFACTURE THEREOF

This application is a divisional of U.S. Ser. No. 11/583,282, filed Oct. 18, 2006 now U.S. Pat. No. 7,884,208, which claims the benefit of U.S. Provisional Application No. 60/728,657, filed Oct. 19, 2005, the entire contents of each of which are hereby incorporated by reference.

Throughout this application various publications, published patent applications, and published patents are referenced. The disclosures of these publications in their entireties are hereby incorporated by reference into this application in order to more fully describe the state of the art to which this invention pertains.

BACKGROUND OF THE INVENTION

Laquinimod is a compound which has been shown to be effective in the acute experimental autoimmune encephalomyelitis (aEAE) model (U.S. Pat. No. 6,077,851). Its chemical name is N-ethyl-N-phenyl-1,2,-dihydro-4-hydroxy-5-chloro-1-methyl-2-oxoquinoline-3-carboxamide, and its Chemical Registry number is 248281-84-7. The processes of synthesis of laquinimod and the preparation of its sodium salt are disclosed in U.S. Pat. No. 6,077,851. An additional process of synthesis of laquinimod is disclosed in U.S. Pat. No. 6,875,869.

In the preparation of laquinimod sodium disclosed in U.S. Pat. No. 6,077,851, laquinimod acid was suspended in ethanol, and 5M sodium hydroxide solution was added. After stirring, the resulting precipitate was filtered, washed with ethanol, and dried. The method used to make laquinimod sodium in U.S. Pat. No. 6,077,851 is commonly referred to as a slurry-to-slurry salt formation.

In the slurry-to-slurry salt formation method of laquinimod sodium, the laquinimod sodium is not dissolved in solution. Any solid impurities, if present in the laquinimod sodium suspension, are therefore not removed by filtration.

Applicants have found that the slurry-to-slurry formation of laquinimod sodium usually results in a product contaminated with other compounds and/or metals. Disclosed is a process for the preparation of laquinimod sodium which addresses this.

SUMMARY OF THE INVENTION

Disclosed is a process for the preparation of laquinimod sodium which removes the impurities present after the salt formation step, thus resulting in crystals of higher purity as well as crystals having improved crystalline characteristics.

The subject invention provides a mixture of crystalline laquinimod sodium particles, wherein 10% or more of the total amount by volume of the laquinimod sodium particles have a size of greater than 40 microns.

The subject invention also provides a mixture of crystalline laquinimod sodium particles, having a tapped density of at least 0.6 g/mL.

The subject invention also provides a composition comprising laquinimod sodium and no more than 2 ppm of a heavy metal calculated based on the total amount of laquinimod sodium in the composition.

The subject invention also provides a process of recrystallization of laquinimod sodium comprising:
a) dissolving laquinimod sodium in water to form an aqueous solution;
b) concentrating the aqueous solution to form a concentrated solution;
c) adding a water-miscible anti-solvent to the concentrated solution to form laquinimod sodium crystals; and
d) isolating the laquinimod sodium crystals.

The subject invention also provides a process for making a pharmaceutical composition comprising laquinimod sodium comprising:
a) obtaining a batch of laquinimod sodium;
b) determining whether insoluble matter is present in the batch of step a) by mixing a sample from the batch in deionized water at room temperature at a ratio of at least 110 mg of sample to 1.0 ml of water, and inspecting the resulting mixture for the presence of insoluble matter; and
c) mixing the batch of step a) with at least one pharmaceutically acceptable carrier if in step b) insoluble matter is determined to be present below a predetermined amount.

DETAILED DESCRIPTION OF THE INVENTION

Figure 1:
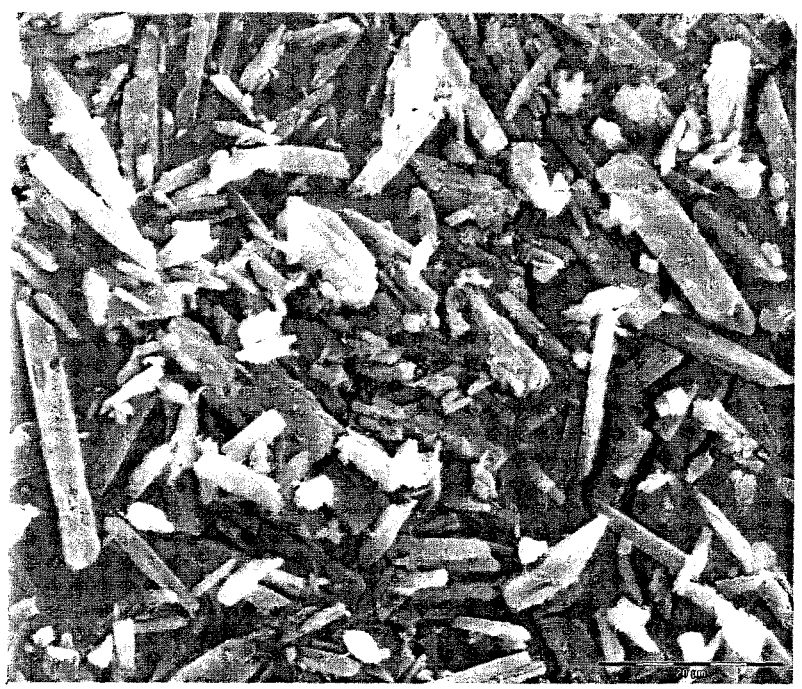
FIG. 1: Scanning electron micrograph of laquinimod sodium prepared according to Example 1 (batch B) from Example 14, before recrystallization.
Figure 2:
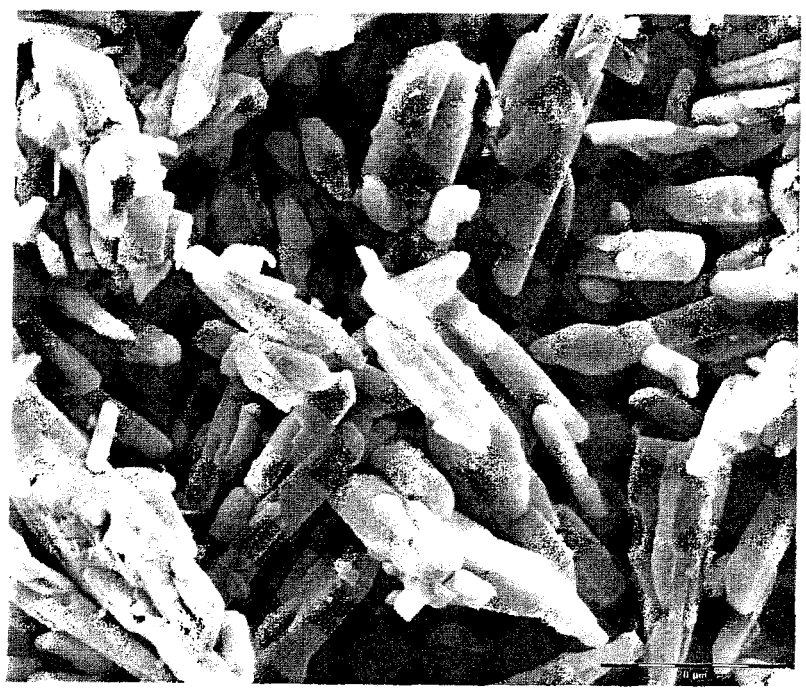
FIG. 2: Scanning electron micrograph of recrystallized crystals from Example 15.
Figure 3:
FIG. 3: Scanning electron micrograph of recrystallized crystals from Example 16.

The subject invention provides a mixture of crystalline laquinimod sodium particles, wherein 10% or more of the total amount by volume of the laquinimod sodium particles have a size of greater than 40 microns.

In an embodiment of the mixture, 50% or more of the total amount by volume of the laquinimod sodium particles have a size of greater than 15 microns.

In a further embodiment, the mixture has a tapped density of at least 0.6 g/mL, at least 0.5 g/mL, or at least 0.4 g/mL.

In another embodiment, the mixture has a bulk density of at least 0.4 g/mL, at least 0.3 g/mL, or at least 0.2 g/mL.

In yet another embodiment, the mixture has a tapped density of less than 0.8 g/mL, or less than 0.7 g/mL.

In a further embodiment, the mixture comprises no more than 2 ppm of a heavy metal. The heavy metal may be iron, nickel or chromium.

In an embodiment, the mixture comprises no more than 2 ppm of iron, no more than 1.5 ppm of iron, or no more than 1 ppm of iron.

In a further embodiment, the mixture comprises no more than 0.2 ppm of nickel, no more than 0.15 ppm of nickel, or no more than 0.1 ppm of nickel.

In yet a further embodiment, the mixture comprises no more than 0.3 ppm of chromium, no more than 0.25 ppm of chromium, no more than 0.2 ppm of chromium, no more than 0.15 ppm of chromium, or no more than 0.1 ppm of chromium.

The subject invention also provides a pharmaceutical composition comprising any of the disclosed mixtures and a pharmaceutically acceptable carrier. The pharmaceutical composition may be in the form of a tablet or capsule.

The subject invention also provides a composition comprising laquinimod sodium and no more than 2 ppm of a heavy metal calculated based on the total amount of laquinimod sodium in the composition. The heavy metal may be iron, nickel or chromium.

In an embodiment, the iron content of the composition is no more than 2 ppm, no more than 1.5 ppm, or no more than 1 ppm.

In a further embodiment of the composition, the nickel content is no more than 0.2 ppm, no more than 0.15 ppm, or no more than 0.1 ppm.

In yet a further embodiment of the composition, the chromium content is no more than 0.3 ppm, no more than 0.25 ppm, no more than 0.2 ppm, no more than 0.15 ppm, or no more than 0.1 ppm.

In another embodiment, the composition is in crystalline form. A composition in the crystalline form may be in the form of any of the disclosed embodiments.

The subject invention also provides a process of recrystallization of laquinimod sodium comprising:
- a) dissolving laquinimod sodium in water to form an aqueous solution;
- b) concentrating the aqueous solution to form a concentrated solution;
- c) adding a water-miscible anti-solvent to the concentrated solution to form laquinimod sodium crystals; and
- d) isolating the laquinimod sodium crystals.

In an embodiment of the process, step a) is performed by heating the aqueous solution to a temperature of 40-80° C.

In a further embodiment of the process, the concentrated solution comprises 1-4 milliliters of water per gram of laquinimod sodium.

In a further embodiment of the process, the concentrated solution comprises 1-2 milliliters of water per gram of laquinimod sodium.

In another embodiment of the process, the anti-solvent is one, or a mixture of more than one, of the group consisting of ethanol, isopropanol, and acetone.

In another embodiment of the process, the anti-solvent is acetone.

In yet another embodiment of the process, the anti-solvent is added in an amount between 3 and 15 milliliters per gram of laquinimod sodium.

In a further embodiment of the process, step c) is followed by cooling the solution to a temperature of below 10° C.

In yet a further embodiment of the process, step b) is followed by seeding the concentrated solution with laquinimod sodium.

The subject invention also provides laquinimod sodium prepared by any one of the disclosed processes.

A process for making a pharmaceutical composition comprising laquinimod sodium comprising:
- a) obtaining a batch of laquinimod sodium;
- b) determining whether insoluble matter is present in the batch of step a) by mixing a sample from the batch in deionized water at room temperature at a ratio of at least 110 mg of sample to 1.0 ml of water, and inspecting the resulting mixture for the presence of insoluble matter; and
- c) mixing the batch of step a) with at least one pharmaceutically acceptable carrier if in step b) insoluble matter is determined to be present below a predetermined amount.

In one embodiment of the process, if insoluble matter in the mixture of step b) is determined not to be present below a predetermined amount, the process further comprises:
- d) dissolving the batch of step a) in water to form an aqueous solution;
- e) filtering the aqueous solution of step d) to reduce the amount of insoluble matter to below the predetermined amount;
- f) concentrating the aqueous solution of step e) to form a concentrated solution;
- g) adding a water-miscible anti-solvent to the concentrated solution of step f) to form laquinimod sodium crystals; and
- h) isolating the laquinimod sodium crystals of step g).

As used herein, a "pharmaceutically acceptable" component is one that is suitable for use with humans and/or animals without undue adverse side effects (such as toxicity, irritation, and allergic response) commensurate with a reasonable benefit/risk ratio.

Thus, a "pharmaceutically acceptable carrier" is a pharmaceutically acceptable solvent, suspending agent or vehicle, for delivering the instant compounds to the animal or human. The carrier is selected with the planned manner of administration in mind. Liposomes are also a pharmaceutical carrier.

A dosage unit may comprise a single compound or mixtures of compounds thereof. A dosage unit can be prepared for oral dosage forms, such as tablets, capsules, pills, powders, and granules.

Drug substance can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral administration. The drug substance can be administered alone but are generally mixed with a pharmaceutically acceptable carrier, and co-administered in the form of a tablet or capsule, liposome, or as an agglomerated powder. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents flow-inducing agents, and melting agents.

Specific examples of the techniques, pharmaceutically acceptable carriers and excipients that may be used to formulate oral dosage forms of the present invention are described, e.g., in U.S. Patent Application Publication No. 2005/0192315. For instance, the oral dosage form of the present invention may comprise an alkaline-reacting component, said component preferably amounting from about 1 to 20% by weight of the formulation in order to keep the pH above 8.

General techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

As used herein, an "anti-solvent" is a solvent in which laquinimod sodium is slightly soluble, very slightly soluble, practically insoluble, or insoluble at room temperature (20-25° C.). The solubility terms are defined below, in accordance with the United States Pharmacopoeia XXV.

| Term | Parts of solvent required for 1 part solute |
| --- | --- |
| Slightly soluble | From 100 to 1000 |
| Very slightly soluble | From 1000 to 10,000 |
| Practically insoluble | 10,000 and over |
| Insoluble | 10,000 and over |

As used herein, "density" is a measurement defined as the mass of a substance per unit volume.

As used herein, "bulk density" or "BD" refers to a density measurement of a loose, uncompacted substance, wherein the volume of the substance includes the air trapped between particles.

As used herein, "tapped density" or "TD" refers to a density measurement of a substance that has been tapped or vibrated, thus minimizing the volume of the substance by eliminating or minimizing the air trapped between particles.

The purification of impure crystalline compounds is usually attained by recrystallization from a suitable solvent or mixture of solvents. (Vogel's Textbook of Practical Organic Chemistry. 5$^{th}$ edition. Longman Scientific & Technical, 1989.) The recrystallization process generally comprises the following steps: a) dissolving the impure crystalline substance in a suitable solvent near the boiling point; b) filtering the hot solution from particles of insoluble material and dust; c) allowing the hot solution to cool to cause the dissolved substance to crystallize out; and d) separating the crystals from the supernatant solution. (Id.)

However, standard recrystallization techniques were accompanied by low or no yields when applied to laquinimod sodium. As shown in Examples 1-10, attempts to recrystallize laquinimod sodium resulted in poor yields, if any. The present invention provides an industrially reproducible recrystallization process that results in high yields of laquinimod sodium.

The process of the present invention uses an anti-solvent in which laquinimod sodium is practically insoluble. In addition, the process of the present invention concentrates the laquinimod sodium aqueous solution before the addition of the anti-solvent.

The laquinimod sodium manufactured by the recrystallization processes of the present invention has increased purity over the laquinimod sodium disclosed in the prior art. U.S. Pat. No. 6,875,869 discloses a process of preparing the base compound laquinimod in high yield and low level of impurities. However, the process in U.S. Pat. No. 6,875,869 is only for synthesis of the base compound and not the salt. As such, the slurry-to-slurry salt formation process would still be needed to form the sodium salt. The slurry-to-slurry salt formation process previously disclosed is not efficient in removing any impurities present in the starting material.

A second advantage of the recrystallization process of the present invention is environmentally-friendliness, as water is used as the primary solvent.

A third advantage of the recrystallization process of the present invention is that laquinimod sodium crystals of a higher density than the laquinimod sodium crystals disclosed in the prior art are produced. Low tapped density is anathema to certain prized qualities in a drug substance such as compressibility, the ability of a powder to decrease in volume under pressure, and compactibility, the ability of a powder to be compressed into a tablet of certain strength or hardness. Crystals with low tapped density are also known to have poor flowability, which results in a lack of uniformity of content in finished dosage forms, especially in tablets. (Rudnic et al. Chpt. 45, *Remington's Pharmaceutical Sciences,* 20$^{th}$ Edition, Lippincott Williams & Wilkins, Baltimore, Md. (2000)) Problems of uniformity of content are especially important in tablets in which the amount of active pharmaceutical ingredient within the tablet is low.

A fourth advantage of the recrystallization process of the present invention is that the resulting laquinimod sodium crystals have increased particle size. Larger particles of laquinimod sodium are more processable when making pharmaceutical compositions. Smaller particles are often associated with dust-like properties which may interfere with processing in manufacture of pharmaceutical compositions. In addition, smaller particles are sometimes associated with flowability problems which may interfere with the manufacture of pharmaceutical compositions. Furthermore, in some instances, chemical stability has been shown to be decreased by the increase in surface area that results from smaller particle size. (Felmeister, A. Chpt 88, *Remington's Pharmaceutical Sciences,* 15$^{th}$ Edition, Mack Publishing Company, Easton, Pa. (1975)).

EXPERIMENTAL DETAILS

Determination of Powder Density
Bulk Density
1. Mix powder;
2. Tare a 50 ml empty cylinder on a 0.01 g sensitivity balance;
3. Transfer the powder, without compacting, to the cylinder being held at approximately a 45 degree angle to achieve an untapped apparent volume of 40 to 50 ml.
4. Bring the cylinder containing the sample to a vertical position by a sharp move in order to level the volume for reading.
5. Read the apparent volume (Va) to the nearest graduated unit;
6. Weigh the cylinder with sample (the balance gives sample weight M);

7. Calculate bulk density in g/ml according to the following equation: BD=M/Va;
8. Perform steps 1-7 again and report the average data of duplicates.

Tapped Density
1. Put the same cylinder used to calculate Bulk Density in a Quantachrome Dual Autotap instrument;
2. Perform 1250 taps;
3. Read the tapped volume (Vf) to the nearest graduated unit;
4. Calculate the tapped density in g/ml according to the following equation: TD=M/Vf;
5. Perform steps 1-4 again and report the average data of duplicates.

Determination of Particle Size

The particle size distributions were measured by Malvern Laser Diffraction, using the Mastersizer S model. Laser diffraction relies on the fact that diffraction angle of light is inversely proportional to particle size. Properties of particles are measured and interpreted as measurements of a sphere (a sphere being the only shape that can be described by one unique number). In addition, laser diffraction calculates a particle size distribution based around volume terms, thus eliminating particle count from the determination of particle size. The Mastersizer S model measures particles using a single technique and a single range setting.

D(0.1) is the particle size, in microns, below which 10% by volume distribution of the population is found. D(0.5) is the particle size, in microns, below which 50% by volume distribution of the population is found. D(0.9) is the particle size, in microns, below which 90% by volume distribution of the population is found.

Determination of Heavy Metals

Metal content was measured using inductively coupled plasma atomic emission spectrometry using an inductively coupled plasma atomic emission spectrometry ("ICP-AES") system manufactured by Spectro (Kleve, Germany). Sample digestion was performed in 65% nitric acid, and the internal standard used was scandium.

Note: In the following examples the volumes of solvents used are calculated relative to starting weight of laquinimod sodium. The yields are calculated in weight percent.

Determination of Purity

Laquinimod sodium and polar impurity/degradation products were determined by isocratic reversed phase high performance liquid chromatography (RP-HPLC), using an ODS-3V column and a mobile phase comprised of a mixture of ammonium acetate buffer at pH 7.0 (80%) and acetonitrile (20%). The detection technique was ultraviolet absorption at 240 nm.

Example 1

Method of Preparing Laquinimod Sodium

Laquinimod acid was prepared according to the method described in U.S. Pat. No. 6,875,869: 5-Chloro-1,2-dihydro-4-hydroxy-1-methyl-2-oxo-quinoline-3-carboxylic acid methyl ester (3.0 g), N-ethylaniline (2 eq 2-2.88 ml), and heptane (60 ml) were heated and the volatiles, mainly heptane and formed methanol, (32 ml) distilled off during 6 hours and 35 minutes. After cooling to room temperature the crystalline suspension was filtered and the crystals were washed with heptane and dried in vacuum to yield laquinimod acid (3.94 g, 98%) as white to off-white crystals.

Laquinimod acid was converted into laquinimod sodium using the method described in U.S. Pat. No. 6,077,851, Example 2: A solution of 5 M sodium hydroxide was prepared by dilution of a 50% by weight sodium hydroxide solution (10.0 g) with sterile water to the total volume of 25 ml. N-Ethyl-N-phenyl-1,2-dihydro-4-hydroxy-5-chloro-1-methyl-2-oxo-quinoline-3-carboxamide (10.0 g) was suspended in ethanol (150 ml) and the previously prepared 5 M sodium hydroxide solution was added to pH of 8-12 (5.6 ml). The reaction mixture was stirred for another 30 minutes at ambient temperature. The resulting precipitation was filtered off and rapidly washed twice with ethanol (2×150 ml). The precipitate was then dried in vacuum over $P_2O_5$ to give the title compound (9.5 g), yield 90%. This process is known as a "slurry-to-slurry process."

Example 2

Laquinimod sodium prepared according to Example 1 was added to 6.1 volumes of water at 50° C. The pH was adjusted to 12.5 by the addition of NaOH and the mixture was stirred until complete dissolution. 50.0 volumes of ethanol were added. The solution was cooled to 2° C. but no crystallization occurred.

Example 3

Laquinimod sodium prepared according to Example 1 was added to 6.1 volumes of water at 50° C. The pH was adjusted to 12.5 by the addition of NaOH and the mixture was stirred until complete dissolution. 100.0 volumes of ethanol were added. The solution was cooled to −18° C. but no crystallization occurred.

Example 4

Laquinimod sodium prepared according to Example 1 was added to 6.1 volumes of water at 50° C. The pH was adjusted to 12.5 by the addition of NaOH and the mixture was stirred until complete dissolution. 50.0 volumes of ethanol were added. The solution was cooled to −18° C. but no crystallization occurred.

Example 5

Laquinimod sodium prepared according to Example 1 was added to 6.1 volumes of water at 50° C. The pH was adjusted to 12.5 by the addition of NaOH and the mixture was stirred until complete dissolution. 50.0 volumes of ethanol were added. The solution was acidified to a pH of 5.0 by the addition of HCl. The solution was cooled to 4° C., and crystallization occurred. The compound which crystallized was filtered and washed with 20 mL of ethanol: water solution 1:1 and was dried at 50° C. under vacuum to a constant weight and was determined to be laquinimod acid, in a yield of 56.2%.

Discussion of Examples 2-5

In Examples 2-5, recrystallization was attempted by dissolving the laquinimod sodium in a small amount of water and by addition of ethanol as an anti-solvent. Although the solubility of laquinimod sodium in ethanol is low (laquinimod sodium is slightly soluble in ethanol at room temperature), nevertheless, no crystallization of laquinimod sodium was attained even though large quantities (as much as 100 volumes) of ethanol were added.

Example 6

Laquinimod sodium prepared according to Example 1 was added to 9.9 volumes of water at 76° C. The pH was adjusted to 10.5-11 by the addition of NaOH and the mixture was stirred until complete dissolution. The solution was cooled to 3° C. but no crystallization occurred.

Example 7

Laquinimod sodium prepared according to Example 1 was added to 9.9 volumes of water at 76° C. The pH was adjusted to 10.5-11 by the addition of NaOH and the mixture was stirred until complete dissolution. 30.6 volumes of isopropanol were added. The solution was cooled to 5° C. but no crystallization occurred.

Discussion of Examples 2-7

Example 6 shows that merely cooling an aqueous solution of laquinimod sodium does not cause crystallization. Example 7 shows that addition of isopropanol anti-solvent (laquinimod sodium is very slightly soluble in isopropanol at room temperature) to an aqueous solution of laquinimod sodium does not cause crystallization.

Examples 2-7 show that standard methods of recrystallization were not effective when used for recrystallization of laquinimod, as either no crystallization occurred or low yields were attained.

Example 8

The solution of Example 7 was then concentrated by evaporation under vacuum to 3.8 volumes. A small amount of solid crystallized out of solution. The mixture was cooled at 7° C. overnight. The mixture was filtered, and the solid crystals were washed with 20 ml of isopropanol and were dried at 50° C. under vacuum to a constant weight. The yield was determined to be 11.2%.

Example 9

The filtrate from Example 8 was collected, and 8.2 volumes (relative to starting laquinimod sodium in Example 7) isopropanol were added to the filtrate at room temperature. The filtrate with isopropanol was then cooled to 7° C., and a solid crystallized out of solution. The crystals were washed with 10 ml of isopropanol and were dried at 50° C. under vacuum to a constant weight and the yield was determined to be 29.8% (of starting laquinimod sodium of Example 7.)

Example 10

Laquinimod sodium prepared according to Example 1 was added to 9.9 volumes of water at 76° C. The pH was adjusted to 10.5-11 by the addition of NaOH and the mixture was stirred until complete dissolution. 91 volumes of acetone were added. The solution was cooled to 5° C. and a crystallization of a small amount of solid was noticed. The solid was washed with acetone and filtered and dried at 50° C. under vacuum to a constant weight. The yield was determined to be 10.2%.

Example 11

Laquinimod sodium prepared according to Example 1 was added to 9.9 volumes of water at 76° C. The pH was adjusted to 10.5-11 by the addition of NaOH and the mixture was stirred until complete dissolution. The solution was concentrated to 1.4 volumes using a rotation evaporator.

8.0 volumes of acetone were added to the solution, and crystallization occurred. The mixture was cooled to 7° C. overnight. The solid was filtered and dried at 50° C. under vacuum to a constant weight. The solid was determined to be laquinimod sodium, with a yield of 90.3%.

Discussion of Examples 10 and 11

Example 10 shows that addition of even large amounts of acetone (laquinimod sodium is practically insoluble in acetone at room temperature) to a non-concentrated aqueous solution of laquinimod sodium provides low yields of crystalline laquinimod sodium.

On the other hand, Example 11 shows that if laquinimod sodium aqueous solution is first concentrated, and then anti-solvent is added, the yields of laquinimod sodium crystal are high. Large amounts of anti-solvent are not required to attain high yields in this case.

Example 12

Laquinimod sodium prepared according to Example 1 was added to 11.1 volumes of water at 78° C. The pH was adjusted to 12 by the addition of NaOH and the mixture was stirred until complete dissolution. The solution was concentrated to 1.9 volumes using a rotary evaporator. The solution was transferred to a warmed reactor (jacket temperature 50° C.)

9.5 volumes of acetone were slowly added to the solution, and crystallization occurred. The mixture was cooled to 3° C. and mixed for 1.5 hours in the reactor. The solid was filtered and washed with fresh acetone, and dried at 50° C. under vacuum to a constant weight and was determined to be laquinimod sodium, with a yield of 79.5%.

Example 13

Recrystallization without Seeding 46.7 g of laquinimod sodium prepared by a scaled-up process following the procedure of Example 1 (batch A), and 500 ml of deionized water were introduced into a laboratory glass reactor. The mixture was stirred and heated to 50° C. until complete dissolution of the solids was observed. The solution was filtered through filter paper, and the filter was washed with 10 ml of water and the wash was combined with the filtrate.

The resulting solution was introduced into a laboratory reactor equipped with a vacuum distillation system. The solution was concentrated by evaporation under vacuum (35-38 mbar) to a volume of 112 ml. After evaporation, the pressure was adjusted to atmospheric pressure and the jacket temperature was raised to 50° C., and 295 g of acetone were added to the batch over 2 hours. Solid crystallization was observed during the acetone addition. The batch was cooled to 2° C. and stirred at this temperature for 12 hours. The solid product was isolated by filtration, washed twice with acetone and dried under vacuum at 35-40° C. to constant weight. 35.7 g of dry solid was obtained, yield 76.4%.

The starting material prepared according to Example 1 (batch A) and the dry recrystallized product were sampled and analyzed for particle size distribution, powder density and chemical purity. The results are presented in Table 1:

TABLE 1

Properties and purity of laquinimod sodium, Example 13

| Quality parameters | | Laquinimod Sodium prepared according to Example 1 (batch A) | Re-crystallized product |
|---|---|---|---|
| Particle size distribution by Malvern, micron | d(0.1) | 1.5 | 13.3 |
| | d(0.5) | 7.1 | 51.1 |
| | d(0.9) | 23.2 | 105.1 |
| Powder density, g/ml | BD | 0.166 | 0.498 |
| | TD | 0.347 | 0.758 |
| Heavy metals by ICP, ppm | Fe | 7 | <2 |
| | Ni | 0.6 | <0.5 |
| | Cr | 0.7 | 0.3 |
| Color | | Grey | Off-white |
| Purity by HPLC, area % | Impurity 1, RT = 5.49 | 0.06 | Not detectable |

HPLC = High Performance Liquid Chromatography
RT = Retention Time

The method of Example 13 was accompanied by high yields which are industrially reproducible.

Example 13 shows that the recrystallization process increased the purity of the laquinimod sodium, as the impurity peak 1 was no longer detectable after recrystallization, and the color was changed. In addition, the content of heavy metals Fe, Ni, and Cr was decreased.

In addition, the powder density of the laquinimod sodium was increased, and the size of the particles was also increased.

Example 14

Laquinimod Sodium Recrystallization with Spontaneous Crystallization—Nucleation in Water 71.4 g of laquinimod sodium prepared by a scaled-up process following the procedure of Example 1 (batch B) and 750 ml deionized water were introduced into a laboratory glass reactor. The mixture was stirred and heated to 60° C., and complete dissolution of the solids was observed. The solution was filtered through filter paper, the filter was washed with 36 ml water and the wash was combined with the filtrate.

The resulting solution was introduced into a laboratory reactor equipped with a vacuum distillation system. The batch was concentrated by evaporation under vacuum (37-38 mbar) to a volume of 153 ml. After the evaporation completion, the reactor pressure was adjusted to atmospheric pressure and the jacket temperature was adjusted to 50° C. The batch was stirred for 25 minutes. At this stage spontaneous crystallization of solids was observed. Then 450.5 g acetone was added to the batch over 2 hours. The batch was cooled to 2° C. and stirred at this temperature for 12 hrs, then the solid product was isolated by filtration, washed twice with acetone and dried under vacuum at 35-40° C. to a constant weight. 64.2 g of dry solid was obtained, yield 89.9%.

The starting material prepared according to Example 1 (batch B) and the dry, recrystallized product were sampled and analyzed for particle size distribution, powder density and chemical purity. The results are presented in Table 2:

TABLE 2

Properties and purity of Laquinimod Sodium, Example 14

| Quality parameters | | Laquinimod Sodium prepared according to Example 1 (batch B) | Re-crystallized product |
|---|---|---|---|
| Particle size distribution by Malvern, micron | d(0.1) | 2.1 | 3.5 |
| | d(0.5) | 10.8 | 15.7 |
| | d(0.9) | 35.3 | 43.2 |
| Powder density, g/ml | BD | 0.189 | 0.224 |
| | TD | 0.452 | 0.429 |
| Heavy metals by ICP, ppm | Fe | 4 | <2 |
| | Ni | <0.5 | <0.2 |
| | Cr | 1 | 0.2 |
| Color | | White | White |
| Purity by HPLC, area % | Impurity 1, RT = 5.52 | 0.03 | 0.00 |
| | Impurity 2, RT = 8.48 | 0.05 | 0.01 |
| | Impurity 3, RT = 12.19 | 0.03 | 0.00 |

Example 15

Recrystallization Method with Seeded Crystallization—Controlled Nucleation in Water 25.0 g of laquinimod sodium prepared by a scaled-up process following the procedure of Example 1 (batch C) and 260 ml of deionized water were introduced into a laboratory glass reactor. The mixture was stirred and heated to 60° C., and complete dissolution of the solids was observed. The solution was filtered through filter paper, the filter was washed with 15 ml of water and the wash was combined with the filtrate. The resulting solution was concentrated by evaporation in a rotation evaporator under vacuum (20-25 mbar) to a residual weight of 60.0 g. After the evaporation completion, the residue was introduced into a laboratory glass reactor which was pre-heated to 50° C. (jacket temperature). The batch was seeded with 0.2 g of solid laquinimod sodium and stirred for one hour, and crystallization of solids was observed. Then 157.7 g of acetone were added to the batch over 2 hours. The batch was cooled to 2° C. and stirred for 12 hours. The solid product was isolated by filtration, washed twice with acetone, and dried under vacuum at 35-40° C. to a constant weight. 22.6 g of dry solid was obtained, yield 90.4%.

The starting material prepared according to Example 1 (batch C) and the dry, recrystallized product were sampled and analyzed for particle size distribution, powder density and chemical purity. The results are presented in Table 3:

TABLE 3

Properties and purity of Laquinimod Sodium

| Quality parameters | | Laquinimod Sodium prepared according to Example 1 (batch C) | Re-crystallized product |
|---|---|---|---|
| Particle size distribution by Malvern, micron | d(0.1) | 1.3 | 6.1 |
| | d(0.5) | 5.9 | 21.2 |
| | d(0.9) | 19.4 | 51.8 |
| Powder density, g/ml | BD | 0.158 | No data |
| | TD | 0.362 | No data |
| Heavy metals by ICP, ppm | Fe | 25 | 8 |
| | Ni | 2.9 | 1.1 |
| | Cr | 3.5 | 1.5 |

TABLE 3-continued

Properties and purity of Laquinimod Sodium

| Quality parameters | | Laquinimod Sodium prepared according to Example 1 (batch C) | Re-crystallized product |
|---|---|---|---|
| Color | | Grey | Off-white |
| Purity by HPLC, area % | Impurity 1, RT = 5.49 | 0.02 | Not detectable |
| | Impurity 2, RT = 8.38 | 0.03 | Not detectable |

Discussion of Examples 14 and 15

The methods of Examples 14 and 15 were accompanied by high yields which are industrially reproducible.

Examples 14 and 15 show that the recrystallization process increased the purity of the laquinimod sodium, as the impurity peaks were no longer detectable after recrystallization. In addition, the content of heavy metals Fe, Ni, and Cr was decreased. The crystals which resulted after recrystallization in examples 14 and 15 were larger than the crystals before the recrystallization.

Example 16

Crystallization without Seeding—Nucleation in the Presence of Acetone

Water (532 mL) and laquinimod sodium (52.3 g) were introduced into a laboratory glass reactor (0.5 L). The suspension was heated to 70-73° C. until a clear solution was obtained. The hot solution was cooled to 50° C. and then filtered through a 0.2 micron filter. The filter was washed with 10 ml of water and the wash was combined with the filtrate. The resulting solution was concentrated to a volume of 112 mL in a 1 liter reactor by evaporation while stirring under a vacuum of 30-50 mbar while maintaining the jacket temperature at 60° C., and the temperature of the reactor at about 35-40° C. Immediately after the evaporation completion and adjustment of pressure, acetone (417 mL) was added to the evaporation residue over 2 hours while the jacket temperature was maintained at 50° C. The crystallization mixture was cooled to a temperature of 2° C. over 2 hours and was kept at this temperature for 5-10 hours. The solid formed was collected by filtration and washed twice with 50 mL of acetone. The wet material was dried in a dryer at 30-40° C. under vacuum to give 47.6 gram (90.6% yield) of dried material. The results are presented in Table 4:

TABLE 4

Properties of Laquinimod Sodium, Example 16

| Quality parameters | | Laquinimod Sodium according to Example 1 (batch B) | Re-crystallized product |
|---|---|---|---|
| Particle size distribution by Malvern, micron | d(0.1) | 2.1 | 15.7 |
| | d(0.5) | 10.8 | 65.5 |
| | d(0.9) | 35.3 | 156.4 |
| Color | | White | White |

The crystals produced by the recrystallization process were larger than the crystals of the starting material.

Example 17

Recrystallization of Crude Laquinimod Sodium with Insoluble Impurities

A 55 mg sample of laquinimod sodium prepared by a scaled-up process following the procedure of Example 1 (batch D) was mixed in 0.5 mL of deionized water at ambient temperature. The sample did not completely dissolve in water.

Purification by recrystallization of a sample of the batch was performed as follows:

Water (391 mL) and laquinimod sodium of Example 1 (batch D) (39.1 g) were introduced into a laboratory glass reactor (0.5 L). The suspension was heated by raising the jacket temperature to 73° C. After 20 min the solution was not clear. The suspension was warmed further by raising the jacket temperature to 75° C. and a clear solution was still not obtained. The hot solution was cooled to 50° C. and filtered through laboratory filter paper over a Buchner funnel. 0.3 grams of solid residue remained on the filter paper. A sample of the solid residue was tested for impurity content. The filter papers were washed with 47 ml of water and the wash was combined with the filtrate. The resulting solution was cooled by lowering the jacket temperature to 25° C. and the solution was then concentrated under vacuum (P<45 mmHg) while heating over the course of 30 min by raising the jacket temperature to 65° C. After completion of evaporation, the residue (82.1 ml, 93.2 g, d=1.135 g/ml) was cooled by lowering the jacket temperature to 50° C. and agitated for 10 min. The batch was then seeded with solid laquinimod sodium and was stirred while maintaining the jacket temperature at 50° C. for 1 hour. Acetone (316.7 mL, 250.2 g) was then added to the crystallizing mixture over 2 hours at 50° C. The resulting suspension was cooled to 2° C. over 4 hours and kept at this temperature for another 11 hours. The solid formed was collected by filtration and was washed twice with 31.3 g of acetone. The wet material was dried in a dryer at 30-40° C. under vacuum to yield 31.7 gram (81.1%) of dried crystalline laquinimod sodium. The impurity content of the crude laquinimod sodium was tested by ICP before and after recrystallization.

TABLE 5

Impurity content in PPM of Laquinimod Sodium

| Impurity | Laquinimod Sodium prepared according to Example 1 (batch D) | Re-crystallized product | Solid Residue |
|---|---|---|---|
| Al | 14.0 | 5.6 | 411 |
| Ca | 165 | 65 | 860 |
| Cr | 2.6 | <0.5 | 99 |
| Cu | 2.8 | 1.3 | 64 |
| Fe | 31.5 | 5.8 | 1544 |
| Ni | 5.5 | <0.5 | 69 |
| S | 466 | <1 | 193 |
| Zn | 20.5 | 7.5 | 352 |

Discussion of Example 17

Even though crude laquinimod sodium had high insoluble impurity levels before recrystallization, the recrystallization process had lowered the impurity levels. The high impurity content in the solid residue shows the importance of filtration of aqueous laquinimod solution in order to lower levels of impurities. Thus it is desirable to lower the amount of insoluble matter to below an amount that has been predetermined to cause deleterious effects on, e.g., stability of the laquinimod formulation.

What is claimed:

1. A process of recrystallization of laquinimod sodium comprising:
   a) dissolving laquinimod sodium in water to form an aqueous solution;
   b) concentrating the aqueous solution to form a concentrated solution;
   c) adding acetone to the concentrated solution to form laquinimod sodium crystals; and
   d) isolating the laquinimod sodium crystals,
wherein step a) is performed by heating the aqueous solution to a temperature of 40-80° C. and wherein the concentrated solution in step b) comprises 1-4 milliliters of water per gram of laquinimod sodium.

2. The process of claim 1, further comprising step aa) after step a) and before step b), said step aa) comprising filtering the aqueous solution to remove solid impurities.

3. The process of claim 1 wherein the concentrated solution comprises 1-2 milliliters of water per gram of laquinimod sodium.

4. The process of claim 1 wherein the anti-solvent is added in an amount between 3 and 15 milliliters per gram of laquinimod sodium.

5. The process of claim 1 wherein step b) is followed by cooling the concentrated solution to a temperature of below 10° C.

6. The process of claims 2 wherein step aa) is followed by seeding the concentrated solution with laquinimod sodium.

7. A mixture of laquinimod sodium prepared by the process of claim 1, wherein the mixture comprises no more than 2 ppm of a heavy metal calculated based on total amount of laquinimod sodium in the mixture, wherein the heavy metal is iron, nickel, chromium or a mixture thereof, and the iron content is no more than 2 ppm, the nickel content is no more than 0.2 ppm and the chromium content is no more than 0.3 ppm.

8. A process for making a pharmaceutical composition comprising laquinimod sodium comprising recrystallizing laquinimod sodium by:
   a) dissolving laquinimod sodium in water to form an aqueous solution;
   b) concentrating the aqueous solution to form a concentrated solution;
   c) adding acetone to the concentrated solution to form laquinimod sodium crystals; and
   d) isolating the laquinimod sodium crystals,
wherein step a) is performed by heating the aqueous solution to a temperature of 40-80° C. and wherein the concentrated solution in step b) comprises 1-4 milliliters of water per gram of laquinimod sodium.

9. The process of claim 8, further comprising step aa) after step a) and before step b), said step aa) comprising filtering the aqueous solution to remove solid impurities.

10. The process of claim 8 wherein the acetone is added in an amount between 3 and 15 milliliters per gram of laquinimod sodium.

11. The process of claim 8 wherein step b) is followed by cooling the concentrated solution to a temperature of below 10° C.

12. The process of claims 9 wherein step aa) is followed by seeding the concentrated solution with laquinimod sodium.

13. The pharmaceutical composition comprising laquinimod sodium prepared by the process of claim 8 having no more than 2 ppm of a heavy metal calculated based on total amount of laquinimod sodium in the composition, wherein the heavy metal is iron, nickel, chromium or a mixture thereof, and the iron content is no more than 2 ppm, the nickel content is no more than 0.2 ppm and the chromium content is no more than 0.3 ppm.

14. The process of claim 8, wherein the resulting laquinimod sodium crystals have reduced levels of polar impurities.

15. The process of claim 8, wherein the resulting laquinimod sodium crystals have reduced levels of a polar impurity having an approximate retention time of 5.52 minutes when determined by isocratic reversed phase HPLC, using an ODS-3V column and a mobile phase comprised of a mixture of ammonium acetate buffer at pH 7.0 (80%) and acetonitrile (20%).

16. The process of claim 8, wherein the resulting laquinimod sodium crystals have reduced levels of a polar impurity having an approximate retention time of 8.48 minutes when determined by isocratic reversed phase HPLC, using an ODS-3V column and a mobile phase comprised of a mixture of ammonium acetate buffer at pH 7.0 (80%) and acetonitrile (20%).

17. The process of claim 8, wherein the resulting laquinimod sodium crystals have reduced levels of a polar impurity having an approximate retention time of 12.19 minutes when determined by isocratic reversed phase HPLC, using an ODS-3V column and a mobile phase comprised of a mixture of ammonium acetate buffer at pH 7.0 (80%) and acetonitrile (20%).

18. The process of claim 8,
   i) wherein step a) is performed by dissolving an amount of laquinimod sodium in water by stirring and heating a mixture of laquinimod sodium and approximately 11 mL of water per gram of laquinimod sodium to 50° C. until complete dissolution of laquinimod sodium and filtering the resulting solution through filter paper, washing the filter paper with water, and combining the wash with the filtrate to form an aqueous solution;
   ii) wherein step b) is performed by concentrating the aqueous solution of step a) by evaporation under vacuum of 35-38 mbar to form a concentrated solution having approximately 2.4 mL of water per gram of laquinimod sodium;
   iii) wherein step c) is performed by allowing the concentrated solution of step b) to equilibrate to atmospheric pressure, heating the concentrated solution to 50° C., adding acetone in an amount approximately 6.3 times the amount of laquinimod sodium to the concentrated solution over 2 hours, cooling the resulting mixture to 2° C. and stirring for 12 hours to produce laquinimod sodium crystals;
   iv) wherein step d) is performed by isolating the laquinimod sodium crystals of step c) by filtration, washing the resulting filtered laquinimod sodium crystals twice with acetone and drying under vacuum at 35-40° C. to constant weight of the laquinimod sodium crystals.

19. The process of claim 8,
   i) wherein step a) is performed by dissolving an amount of laquinimod sodium in water by stirring and heating a mixture of laquinimod sodium and approximately 11 mL of water per gram of laquinimod sodium to 60° C. until complete dissolution of laquinimod sodium and filtering the resulting solution through filter paper, washing the filter paper with water, and combining the wash with the filtrate to form an aqueous solution;
   ii) wherein step b) is performed by concentrating the aqueous solution of step a) by evaporation under vacuum of 37-38 mbar to form a concentrated solution having approximately 2.1 mL of water per gram of laquinimod sodium;

iii) wherein step c) is performed by allowing the concentrated solution of step b) to equilibrate to atmospheric pressure, heating the concentrated solution to 50° C., stirring the concentrated solution for 25 minutes, adding acetone in amount approximately 6.3 times the amount of laquinimod sodium to the concentrated solution over 2 hours, cooling the resulting mixture to 2° C. and stirring for 12 hours to produce laquinimod sodium crystals;

iv) wherein step d) is performed by isolating the laquinimod sodium crystals of step c) by filtration, washing the filtered laquinimod sodium crystals twice with acetone and drying under vacuum at 35-40° C. to constant weight of the laquinimod sodium crystals.

20. The process of claim 8, i) wherein step a) performed by dissolving an amount of laquinimod sodium in water by stirring and heating a mixture of laquinimod sodium and approximately 10 mL of water per gram of laquinimod sodium to 60° C. until complete dissolution of laquinimod sodium and filtering the resulting solution through filter paper, washing the filter paper with water, and combining the wash with the filtrate to form an aqueous solution;

ii) wherein step b) is performed by concentrating the aqueous solution of step a) by evaporation under vacuum of 20-25 mbar to form a concentrated solution having a residual weight of approximately 2.4 times the amount of laquinimod sodium;

iii) wherein step c) is performed by transferring the concentrated solution of step b) to a vessel pre-heated to 50° C. and seeding the transferred solution with solid laquinimod sodium, stirring for one hour, adding acetone in an amount approximately 6.3 times the amount of laquinimod sodium to the concentrated solution over 2 hours, cooling the resulting mixture to 2° C. and stirring for 12 hours to produce laquinimod sodium crystals;

iv) wherein step d) is performed by isolating the laquinimod sodium crystals of step c) by filtration, washing the filtered laquinimod sodium crystals twice with acetone and drying under vacuum at 35-40° C. to constant weight of the laquinimod sodium crystals.

21. The process of claim 8, i) wherein step a) is performed by dissolving an amount of laquinimod sodium in water by heating a mixture of laquinimod sodium in approximately 10 mL of water per gram of laquinimod sodium to 70-73° C. to form a clear solution, then cooling the clear solution to 50° C., filtering the cooled solution through a 0.2 micron filter, washing the filter with water, and combining the wash with the filtrate to form an aqueous solution;

ii) wherein step b) is performed by concentrating the aqueous solution of step a) by evaporation in a jacketed reactor under vacuum of 30-50 mbar while maintaining the temperature of the jacket at 60° C. and maintaining the temperature of the reactor at about 35-40° C. to form a concentrated solution having approximately 2.1 mL of water per gram of laquinimod sodium;

iii) wherein step c) is performed by allowing the concentrated solution of step b) to equilibrate to atmospheric pressure, adding acetone in an amount approximately 8 times the amount of laquinimod sodium to the concentrated residue over 2 hours while maintaining the jacket temperature at 50° C., cooling the resulting mixture to 2° C. over 2 hours and keeping the mixture at this temperature for 5-10 hours to produce laquinimod sodium crystals;

iv) wherein step d) is performed by isolating the laquinimod sodium crystals of step c) by filtration, washing the filtered laquinimod sodium crystals twice with acetone and drying under vacuum at 30-40° C.

22. The process of claim 8, i) wherein step a) is performed by dissolving an amount of laquinimod sodium in water by heating a mixture of laquinimod sodium and approximately 10 mL of water per gram of laquinimod sodium to 75° C., cooling the resulting solution to 50° C., filtering the cooled solution through a filter, washing the filter with water, and combining the wash with the filtrate in a jacketed reactor to form an aqueous solution;

ii) wherein step b) is performed by cooling the aqueous solution of step a) by lowering the jacket temperature to 25° C., concentrating said aqueous solution of step a) by evaporation in the jacketed reactor under vacuum of less than 45 mmHg while heating for 30 minutes by raising the jacket temperature to 65° C. to form a concentrated solution having approximately 2.1 mL of water per gram of laquinimod sodium;

iii) wherein step c) is performed by cooling the concentrated solution of step b) by lowering the jacket temperature to 50° C. and agitating for 10 minutes, seeding the resulting solution with solid laquinimod sodium and stirring while maintaining the jacket temperature at 50° C. for 1 hour, adding acetone in an amount approximately 8 times the amount of laquinimod sodium to the resulting mixture over 2 hours at 50° C., cooling the resulting mixture to 2° C. over 4 hours and maintaining the temperature of the mixture at 2° C. for 11 additional hours to form laquinimod sodium crystals;

iv) wherein step d) is performed by isolating the laquinimod sodium crystals of step c) by filtration, washing the filtered laquinimod sodium crystals twice with acetone and drying under vacuum at 30-40° C.

23. The process of claim 8, further comprising step e) after step d), wherein said step e) comprising preparing a powder or granules from the isolated laquinimod sodium crystals of step d).

* * * * *